United States Patent [19]

Karrer

[11] 4,412,021
[45] Oct. 25, 1983

[54] NOVEL POLYALKYLPIPERIDYL-UREAS AND THEIR USE AS STABILIZERS

[75] Inventor: Friedrich Karrer, Zofingen, Switzerland

[73] Assignee: Ciba-Geigy Corporation, Ardsley, N.Y.

[21] Appl. No.: 351,577

[22] Filed: Feb. 23, 1982

Related U.S. Application Data

[63] Continuation of Ser. No. 158,038, Jun. 9, 1980, abandoned.

[30] Foreign Application Priority Data

Jun. 21, 1979 [CH] Switzerland ............. 5807/79

[51] Int. Cl.³ ............... C08K 5/34; C07D 211/56; C07D 211/92
[52] U.S. Cl. ............... 524/102; 524/99; 546/187; 546/190; 546/244; 546/245
[58] Field of Search ............... 546/187, 190, 244, 245; 524/99, 102

[56] References Cited

U.S. PATENT DOCUMENTS

| | | | |
|---|---|---|---|
| 3,684,765 | 8/1972 | Matsui et al. | 524/99 |
| 4,166,813 | 9/1979 | Soma et al. | 524/102 |
| 4,191,683 | 3/1980 | Brunetti et al. | 546/224 |
| 4,223,147 | 9/1980 | Oertel et al. | 524/102 |
| 4,260,689 | 4/1981 | Rody et al. | 524/102 |

*Primary Examiner*—John Kight, III
*Assistant Examiner*—Kriellion Morgan
*Attorney, Agent, or Firm*—Harry Falber

[57] ABSTRACT

Polyalkylpiperidyl-ureas of the formula I

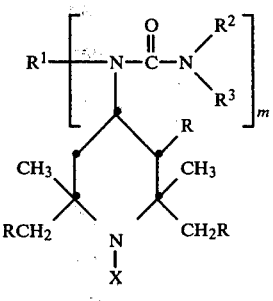

in which m is 1–4, X, $R^2$ and $R^3$ are monovalent substituents and $R^1$ is a m-valent radical, can be prepared from the corresponding 4-aminopiperidines by reaction with carbamoyl chlorides. They are outstanding stabilizers for plastics, and especially for polyolefins, to protect them against degradation by the action of light.

7 Claims, No Drawings

NOVEL POLYALKYLPIPERIDYL-UREAS AND THEIR USE AS STABILIZERS

This is a continuation of application Ser. No. 158,038, filed on June 9, 1980, now abandoned.

The invention relates to novel substituted ureas which have at least one polyalkylpiperidine radical as a substituent and are valuable stabilisers for plastics, especially to protect these against damage by light.

Ureas containing polyalkylpiperidine substituents and their use as stabilisers are already known. Thus, German Offenlegungsschrift No. 2,040,975 described derivatives of 4-amino-2,2,6,6-tetramethyl-piperidine of the formula

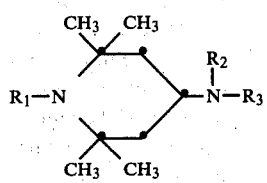

in which $R_1$ is H or an acyl group, $R_2$ is H or a monovalent radical and $R_3$ inter alia can be a carbamoyl group or a N-substituted carbamoyl group, for example, —$CONH_2$, —CONH-alkyl, —CONH-cycloakyl or —CONH-aryl.

German Offenlegungsschrift No. 2,349,962 described similar compounds of the following formula

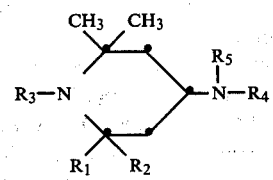

in which $R_1$ and $R_2$ are alkyl radicals, $R_3$ is alkyl, alkenyl, alkynyl or aralkyl, $R_5$ is H or a monovalent radial and $R_4$ inter alia is a N-substituted or unsubstituted carbamoyl group, for example —$CONH_2$, —CONH-alkyl, —CONH-aryl or —CONH-aralkyl. The urea derivatives disclosed in these two patent specifications carry at least one hydrogen atom either on the nitrogen in the 1-position or on the nitrogen in the 3-position of the urea grouping. Examples are 1-benzyl-3-(1,2,2,6,6-pentamethyl-4-piperidyl)-urea or 1,1-dimethyl-3-(1,2,2,6,6-pentamethyl-4-piperidyl)-urea. These compounds are good light stabilisers for plastics if these are processed at low temperatures. At higher processing temperatures, a more or less discernible discoloration and a relatively weak stabiliser action result.

It has been found that polyalkylpiperidylureas in which the urea group does not carry a hydrogen atom either on the nitrogen in the 1-position or on the nitrogen in the 3-position possess a considerably superior action as light stabilisers. In certain substrates their light stabilising action is superior to that of most of the known light stabilisers, i.e. including those of a chemically completely different constitution.

The invention therefore relates to compounds of the formula I

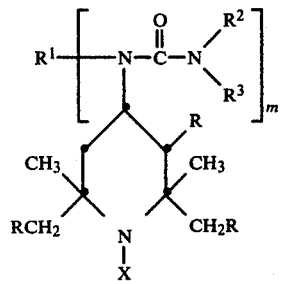

in which m is 1, 2, 3 or 4, X is H, O, $C_1$-$C_{18}$-alkyl, $C_3$-$C_5$-alkenyl, propargyl, $C_7$-$C_{12}$-phenylalkyl or a group of the formula —CO—$C_1$—$C_8$-alkyl, —CO—$C_2$-$C_3$-alkenyl, —CO—O—$C_1$-$C_{10}$-alkyl or —CO—N—($C_1$-$C_{10}$-alkyl)$_2$, R is hydrogen or methyl and $R^1$, if m is 1, is $C_1$-$C_{18}$-alkyl, $C_3$-$C_5$-alkenyl, $C_3$-$C_4$-alkynyl, $C_5$-$C_6$-cycloalkyl, $C_7$-$C_{18}$-aralkyl, $C_6$-$C_{12}$-aryl or a group of the formula II

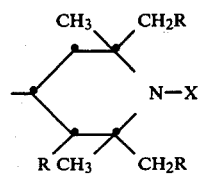

or, if m is 2, is $C_2$-$C_{20}$-alkylene, $C_4$-$C_{12}$-mono- or -dioxaalkylene, a

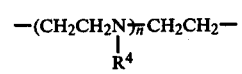

or —$(CH_2)_3$—$N(R^5)$—$(CH_2)_3$-group, cyclohexylene, xylylene, hexahydroxylene, or a

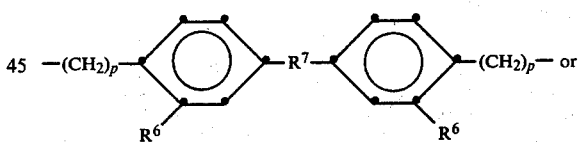

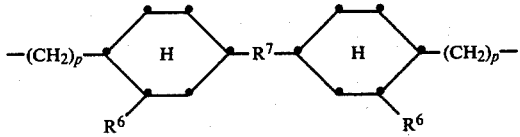

group, in which $R^4$ is hydrogen, $C_1$-$C_4$-alkyl, allyl, benzyl or a

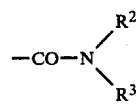

group, n is an integer from 1 to 5, $R^5$ is $C_1$-$C_{12}$-alkyl, phenyl or cyclohexyl, p is nought or 1, $R^6$ is hydrogen or methyl and $R^7$ is —$CH_2$— or >$C(CH_3)_2$, or $R^1$, if m is 3, is a

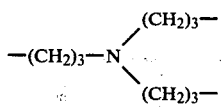

radical and if m is 4 is a radical of the formula

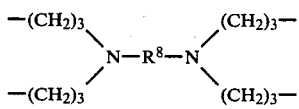

in which $R^8$ is $C_2$–$C_{20}$-alkylene, cyclohexylene or xylylene, and $R^2$ and $R^3$ independently of one another are $C_1$–$C_{12}$-alkyl, cyclohexyl, $C_3$–$C_5$-alkenyl, propargyl, $C_7$–$C_{12}$-phenylalkyl or $C_6$–$C_{12}$-aryl and $R^2$ can also be $C_1$–$C_4$-alkoxy, or $R^2$ and $R^3$ together form $C_4$–$C_9$-alkylene or 3-oxa-1,5-pentylene.

In formula I, X and $R^1$ can e alkyl, for example methyl, ethyl, propyl, butyl, pentyl, isopentyl, hexyl, octyl, 2-ethylhexyl, dodecyl or octadecyl. Alkenyl $R^1$, $R^2$, $R^3$ or X can be, for example, allyl, methallyl or 2-butenyl. Alkynyl $R^1$ can be, for example, propargyl or 2-butynyl.

Phenylalkyl X, $R^2$ and $R^3$ can be, for example, phenylpropyl, phenylbutyl or phenylethyl, but preferably benzyl. As aralkyl, $R^1$ can additionally also be naphthylmethyl.

As an acyl radical —CO—$C_1$–$C_8$-alkyl, X can be, for example, acetyl, propionyl, butyryl, isovaleryl, hexanoyl or octanoyl. As alkoxycarbonyl —CO—O—$C_1$–$C_{10}$-alkyl, X can be, for example, methoxycarbonyl, ethoxycarbonyl or octyloxycarbonyl. As a dislkylcarbamoyl radical —CO—N—($C_2$–$C_{10}$-alkyl)$_2$, X can be, for example, dimethylcarbamoyl, dibutylcarbamoyl or dioctylcarbamoyl.

Cycloalkyl $R^1$ can be cyclopentyl or cyclohexyl. Aryl $R^1$, $R^2$ and $R^3$ can be, for example, phenyl, naphthyl or diphenylyl.

Alkylene $R^1$ can be a branched or unbranched alkylene radical, for example, 1,2-ethylene, 1,2-propylene, 1,3-propylene, 2,2-diethyl-1,3-propylene, tetramethylene, hexamethylene or octa-, deca-, dodeca- or octadeca-methylene. Oxaalkylene $R^1$ can be, for example, 3-oxa-1,5-pentylene, 4-oxa-1,7-heptylene or 4,7-dioxa-1,10-decylene. If $R^2$ and $R^3$ together are $C_4$–$C_9$-alkylene or 3-oxapentylene, they form, together with the N atom to which they are bonded, for example, a pyrrolidine, piperidine, 2,2,6,6-tetramethylpiperidine or morpholine ring.

Preferred compounds of the formula I are those in which R is hydrogen. Further preferred compounds of the formula I are those in which m is 1 or 2, R is hydrogen, X is hydrogen, $C_1$–$C_8$-alkyl, allyl or benzyl and $R^1$, if m is 1, is $C_1$–$C_{12}$-alkyl or a group of the formula II, and, if m is 2, is$C_2$–$C_{10}$-alklyene or $C_4$–$C_6$-oxaalkylene, 1,4-cyclohexylene or a

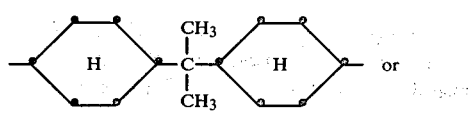 or

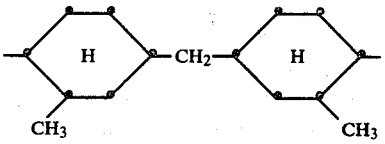

group, and $R^2$ and $R^3$ independently of one another are $C_1$–$C_{10}$-alkyl, phenyl, cyclohexyl, allyl or benzyl, or $R^2$ and $R^3$ together are $C_4$–$C_6$-alkylene or 3-oxa-1,5-pentylene.

Particularly preferred compounds of the formula I are those in which R is hydrogen, X is hydrogen, $C_1$–$C_4$-alkyl, allyl or benzyl and $R^1$, if m is 1, is $C_1$–$C_4$-alkyl or a group of the formula II, and, if m is 2, is $C_2$–$C_6$-alkylene or $C_4$–$C_6$-oxaalkylene, and $R^2$ and $R^3$ are $C_1$–$C_{12}$-alkyl, phenyl, cyclohexyl or allyl, or $R^2$ and $R^3$ together are $C_4$–$C_6$-alkylene or 3-oxa-1,5-pentylene.

Examples of compounds of the formula I in which m is 1 are: 1,1-dimethyl-3,3-di-(2,2,6,6-tetramethyl-4-piperidyl)-urea, 1,1-dibutyl-3,3-di-(2,2,6,6-tetramethyl-4-piperidyl)-urea, 1,1-dibenzyl-3,3-di-(1-benzyl-2,2,6,6-tetramethyl-4-piperidyl)-urea, 1,1,3-trimethyl-3-(1,2,2,6,6-pentamethyl-4-piperidyl)-urea, 1,1,3-triethyl-3-(2,2,6,6-tetramethyl-4-piperidyl)-urea, 1,3-dimethyl-1-octyl-3-(tetramethyl-4-piperidyl)-urea, 1,3-dimethyl-1-phenyl-3-(tetramethyl-4-piperidyl)-urea, 1,1-dibutyl-3-cyclohexyl-3-(tetramethyl-4-piperidyl)-urea, 1,2,2,6,6-pentamethyl-4-[(N-piperidinocarbonyl)-methylamino]-piperidine, 1,1-dimethyl-3,3-di-(1-allyl-2,2,6,6-tetramethyl-4-piperidyl)-urea and 1,1,3-trimethyl-3-(1,3,3,6-tetramethyl-2,6-diethyl-4-piperidyl)-urea.

Examples of compounds of the formula I in which m is 2 are: N,N'-bis-(dimethylcarbamoyl)-N,N'-bis-(2,2,6,6-tetramethyl-4-piperidyl)-hexamethylenediamine, N,N'-bis-(dimethylcarbamoyl)-N,N'-bis-(1-allyl-2,2,6,6-tetramethyl-4-piperidyl)-tetramethylenediamine, N,N'-bis-(diethylcarbamoyl)-N,N'-bis-(1-benzyl-2,2,6,6-tetramethyl-4-piperidyl)-2,2,5-trimethyl-hexamethylenediamine, N,N'-bis-(diethylcarbamoyl)-N,N'-bis-(1,2,2,6,6-pentamethyl-4-piperidyl)-dodecamethylenediamine, N,N'-bis-(methyl-phenylcarbamoyl)-N,N'-bis-(1,2,2,6,6-pentamethyl-4-piperidyl)-p-xylylenediamine, $N^1,N^4$-bis-(diethylcarbamoyl)-$N^1,N^4$-bis-(1,2,2,6,6-pentamethyl-4-piperidyl)-$N^2,N^3$-dimethyl-triethylenetetramine, 1,9-bis-(dicyclohexylcarbamoyl)-1,9-bis-(2,2,6,6-tetramethyl-4-piperidyl)-5-methyl-1,5,9-triazanonane, 1,4,7-tris-(dimethylcarbamoyl)-1,7-bis-(2,2,6,6-tetramethyl-4-piperidyl)-1,4,7-triazaheptane, N,N'-bis-(dibutylcarbamoyl)-N,N'-bis-(2,2,6,6-tetramethyl-4-piperidyl)-2,2,-di-(4-aminocyclohexyl)-propane, N,N'-bis-(diphenylcarbamoyl)-N,N'-bis-(1,2,2,6,6-pentamethyl-4-piperidyl)-di-(4-amino-3-methyl-cyclohexyl)-methane and N,N'-bis-(diethylcarbamoyl)-N,N'-bis-(1,2,3,6-tetramethyl-2,6-diethyl-4-piperidyl)-1,9-diaza-5-oxanonane.

The compounds of the formula I can be prepared by various methods. The most important method is the reaction of a 4-aminopiperidine of the formula III with a carbamic acid chloride:

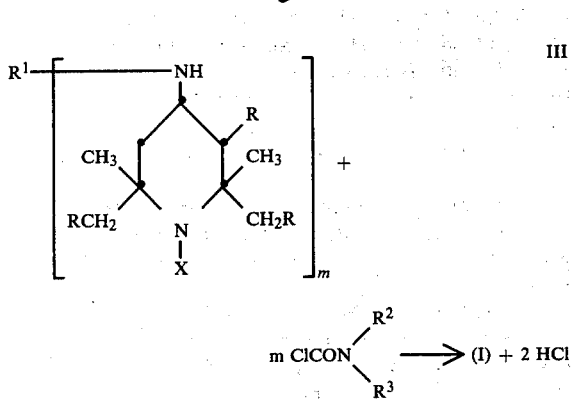

The reaction is carried out in the presence of molar amounts of a HCl acceptor. Suitable HCl acceptors are inorganic or organic bases, for example alkali metal hydroxides, alkali metal carbonates or tertiary amines.

The reaction is preferably carried out in a solvent. Suitable solvents are, for example, chloroform, methylene chloride, benzene, toluene, xylene, tetrahydrofuran, dioxan, dimethoxyethane or dimethylformamide.

A second method is the reaction of III with phosgene, if necessary in the presence of a proton acceptor, followed by the reaction of the resulting carbamoyl chloride IV with a secondary amine:

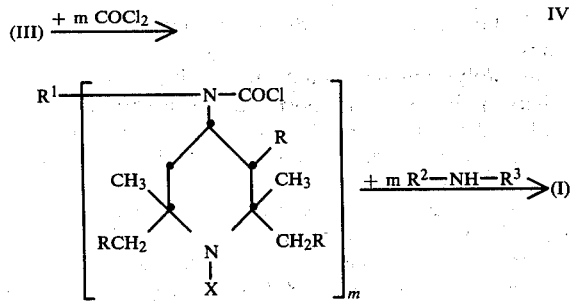

The reaction in the first stage (phosgenation) is effected in an inert solvent, for example benzene, toluene, xylene, chloroform, ethyl acetate or the like, at $-30°$ to $+50°$ C. The intermediate IV does not need to be isolated but can be reacted with the amine immediately after the first stage has ended. The reaction with the amine is effected with the addition of at least 2 mmols of HCl-acceptor. An excess of the secondary amine can also be used for this purpose.

A third process comprises the reaction of III with a N,N-disubstituted urea:

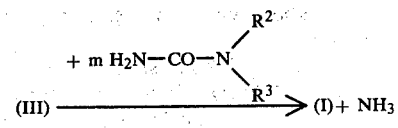

For this reaction, the urea can also be used in excess. The reaction is carried out without a solvent or in a high-boiling, polar solvent, for example dimethylformamide or dimethylsulphoxide, at temperatures of 150° to 250° C. The course of the reaction can be followed by measuring the $NH_3$ formed.

The 4-aminopiperidines of the formula III which are used as a starting material in all three processes can be obtained from the corresponding 4-oxopiperidines by catalytic hydrogenation in the presence of the primary amines $R^1(NH_2)_n$, as is described in German Offenlegungsschriften Nos. 2,040,975 and 2,349,962. If the substituent X is a hydrocarbon or acyl radical, it can be introduced into the corresponding NH compound by the conventional methods for the alkylation or acylation of secondary amines. This introduction of X can be effected at the stage of the 4-oxopiperidines or, preferably, at the stage of the 4-ureidopiperidines. Piperidin-1-oxyls (X=O) can be prepared by oxidising 4-ureido-1-hydrogenopiperidines (formula I, X=H) by means of percarboxylic acids or by means of $H_2O_2$ in the presence of tungsten catalysts.

A further possibility for the preparation of the compounds of the formula I comprises the N-alkylation of trisubstituted or disubstituted ureas of the formula V, VI or VII with the corresponding alkyl, alkenyl or aralkyl halides under the conditions of the phase transfer process:

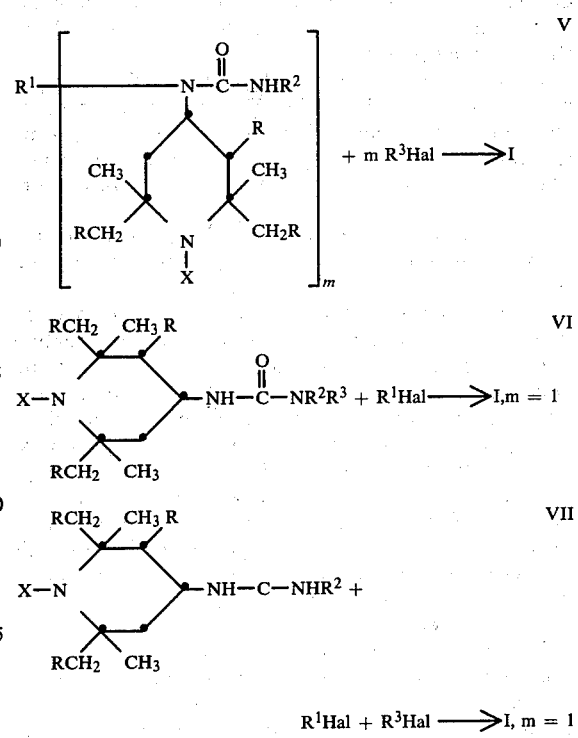

These reactions are carried out in a water-immiscible solvent, for example benzene, toluene, xylene, methylene chloride or dioxan, and an alkali metal hydroxide is added, in powder form or in the form of a concentrated aqueous solution, in a molar amount which corresponds to the amount of halide used. Solid $K_2CO_3$ can also be used. Furthermore, a quaternary ammonium salt, for example benzyl-trimethylammonium chloride, is added in catalytic amounts, as a phase transfer catalyst.

The compounds of the formulae V, VI and VII have been disclosed in German Offenlegungsschriften Nos. 2,040,975 or 2,349,962, which have been mentioned initially, or can be prepared by the methods described in these Offenlegungsschriften. Preferably, the compounds of the formula V, VI or VII which are used are those in which X is not hydrogen. If, however, a compound of the formula V, VI or VII is used in which X is hydrogen, a substituent can be introduced on the piperidine nitrogen at the same time, and a compound of the formla I is obtained in which X is $R^3$ or $R^1$. The reaction of a compound of the formula VII with $R^1$Hal and $R^3$Hal is preferably used when $R^1$ and $R^3$ are identical.

The compounds of the formula I are in most cases crystalline substances which can be purified by recrystallisation. However, their melting points are lower than those of the corresponding ureas which possess CONH groups. Their solubility and compatability in diverse substances is also greater than that of the CONH compounds.

The compounds of the formula I are furthermore distinguished by outstanding stability to hydrolysis, which is far superior to the stability to hydrolysis of the CONH compounds, which in itself is good.

The most valuable characteristic of the compounds of the formula I is their outstanding stabiliser action, in particular against the degradation of organic polymers by the action of light. Examples of polymers which are damaged by the action of light and which can be stabilised by the addition of compounds of the formula I are the following polymers.

1. Polymers of mono- and di-olefins, for example polyethylene (which can be crosslinked), polypropylene, polyisobutylene, polybut-1-ene, polymethylpent-1-ene, polyisoprene or polybutadiene and also polymers of cycloolefins, for example of cyclopentane or norbornene.

2. Mixtures of the polymers mentioned under 1), for example mixtures of polypropylene with polyethylene or with polyisobutylene.

3. Copolymers of mono- and di-olefins with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/ethyl acrylate copolymers, ethylene/alkyl methacrylate copolymers, ethylene/vinyl acetate copolymers or ethylene/acrylic acid copolymers and their salts (ionomers), and also terpolymers of ethylene with propylene and a diene, such as hexadiene, dicyclopentadiene or ethylidenenorbornene.

4. Polystyrene.

5. Statistical copolymers of styrene or α-methylstyrene with dienes or acrylic derivatives, for example styrene/butadiene, styrene/acrylonitrile, styrene/ethyl methacrylate or styrene/acrylonitrile/methacrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene-/styrene or styrene/ethylene-proplyene/styrene.

6. Graft copolymers of styrene, for example styrene on polybutadiene, styrene and acrylonitrile on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, or styrene and acrylonitrile on acrylate/butadiene copolymers, and also mixtures thereof with the copolymers listed under 5), for example those known as ABS, MBS, ASA or AES polymers.

7. Halogen-containing polymers, for example polychloroprene, chlorinated rubber or chlorinated or chlorosulfonated polyethylene, and especially polymers of halogen-containing vinyl compounds, for example polyvinyl chloride, polyvinylidene chloride, polyvinyl fluoride or polyvinylidene fluoride; and also copolymers thereof, such as vinyl chloride/vinylidene chloride, vinyl chloride/vinyl acetate or vinylidene chloride/vinyl acetate.

8. Polymers which are derived from α,β-unsaturated acids and their derivatives, such as polyacrylates and polymethacrylates, polyacrylamides and polyacrylonitriles.

9. Copolymers of the monomers listed under 8), with one another or with other unsaturated monomers, for example acrylonitrile/butadiene copolymers, acrylonitrile/alkyl acrylate copolymers, acrylonitrile/vinyl chloride copolymers or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalklylene glycols, polyethylene oxide or polypropylene oxide or their copolymers with bis-glycidyl ethers.

12. Polyacetals, such as polyoxymethylene, and also those polyoxymethylenes which contain comonomers, for example ethylene oxide.

13. Polyphenylene oxides and polyphenylene sulfides.

14. Polyurethanes which are derived from polyethers, polyesters and polybutadienes with terminal hydroxyl groups on the one hand and from aliphatic or aromatic polyisocyanates on the other hand, and also their precursors.

15. Polyamides and copolyamides which are derived from diamines and dicarboxylic acdis and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene-terephthalamide or poly-m-phenylene-isophthalamide, and also the copolymers thereof with polyethers, for example with polyethylene glycol, polypropylene glycol or polytetramethyl glycol.

16. Polyureas, polyimides and polyamide-imides.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate or polyhydroxybenzoates, and also block polyether-esters which are derived from polyethers with hydroxyl end groups.

18. Polycarbonates.

19. Polysulfones and polyether-sulfones.

20. Crosslinked polymers which are derived from aldehydes on the one hand and from phenols, urea or melamine on the other hand, such as phenol-formaldehyde resins, urea-formaldehyde resins and melamine-formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also their halogen-containing modifications of low combustibility.

23. Crosslinkable acrylic resins which are derived from substituted acrylic acid esters, for example from epoxyacrylates, urethane-acrylates or polyester-acrylates.

24. Alkyd resins, polyester resins and acrylate resins which are crosslinked with melamine resins, urea resins, polyisocyanates or epoxide resins.

25. Crosslinked epoxide resins which are derived from polyepoxides, for example from bis-glycidyl ethers or from cycloaliphatic diepoxides.

26. Naturally occurring polymers, such as cellulose, natural rubber and gelatine, and also their polymer-homologously chemically modified derivatives, such as cellulose acetates, cellulose propionates and cellulose butyrates and the cellulose ethers, such as methylcellulose.

The stabilisation of polyolefins and styrene polymers and of polyurethanes is of particular importance and the compounds of the formula I are outstandingly suitable for this. Examples of such polymers are high density and low density polyethylene, polypropylene, ethylene/propylene copolymers, polystyrene, styrene/butadiene/acrylonitrile copolymers, mixtures of polyolefins or of styrene polymers, and polyurethanes based on polyethers or polyesters, in the form of films, fibres, lacquers, elastomers or foams. The stabilisation of lacquer resins, for example of alkyd resins, polyester resins and acrylic resins and their mixtures with melamine resins, is also of particular importance.

The stabilisers are added to the plastics in a concentration of 0.01 to 5% by weight, based on the material to be stabilised. Preferably 0.03 to 1.5 and particularly preferentially 0.2 to 0.6% by weight of the compounds, based on the material to be stabilised, is incorporated into the latter.

The incorporation can be effected after polymerisation, for example by mixing the compounds, and if desired further additives, into the melt by the methods customary in industry, before or during shaping, or by applying the dissolved or dispersed compounds to the polymer, with subsequent evaporation of the solvent if necessary.

The compounds can also be added to the plastics to be stabilised in the form of a master batch which contains these compounds, for example in a concentration of 2.5 to 25% by weight.

In addition to the compounds of the formula I, yet further known stabilisers can also be added to the plastics. These can be, for example, antioxidants, light stabilisers or metal deactivators or also costabilisers, for example those of the organic phosphite type. Furthermore, other additives customary in plastics technology can be added, for example flame-proofing agents, antistatic agents, plasticisers, lubricants, blowing agents, pigments, reinforcing materials or fillers. Specific examples of such known and conventional additives are listed on pages 25-32 of German Offenlegungsschrift No. 2,349,962.

The invention therefore also relates to the plastics which are stabilised by the addition of 0.01 to 5% by weight of a compound of the formula I and which, if desired, can contain yet further known and conventional additives. The plastics stabilised in this way can be used in very diverse forms, for example as films, fibres, tapes or profiles or as binders for lacquers, adhesives or putties, or as a coating for photograhic films and papers.

The preparation and use of the compounds according to the invention are described in more detail in the following examples. Parts and percentages are by weight. The temperatures are in degrees Centigrade.

EXAMPLE 1

33.9 g (0.315 mol) of dimethylcarbamoyl chloride are added dropwise, with stirring, at 105°-110° C. to a solution of 55 g (0.15 mol) of N,N'-bis-(2,2,6,6-tetramethyl-4-piperidyl)-hexamethylenediamine in 130 ml of xylene and 44.6 g (0.345 mol) of ethyldiisopropylamine and the mixture is stirred for a total of 12 hours at 110°. For working up, the reaction mixture is washed repeatedly with water, dried over sodium sulfate and completely freed from the solvent in vacuo. The crude compound is recrystallised from ligroin (boiling point 110°-140°) and by this means N,N'-bis-dimethylcarbamoyl-N,N'-bis-(2,2,6,6-tetramethylpiperid-4-yl)-hexamethylenediamine with a melting point of 142°-144° is obtained.

(compound No. 1)

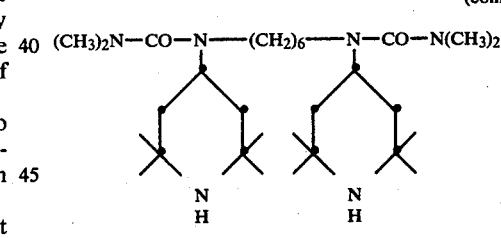

The following compounds are prepared analogously:

---

N—bis-(2,2,6,6-tetramethylpiperid-4-yl)-N'—diethylurea melting point 154-155°
(compound No. 2)

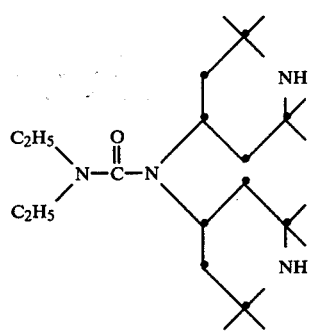

N—bis-(2,2,6,6-tetramethylpiperid-4-yl)-N'—dimethylurea

| | |
|---|---|
| 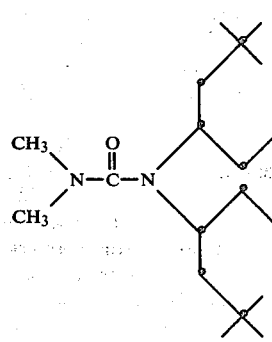 | melting point 137–138° (compound No. 3) |

N,N'—bis-(1,2,2,6,6-pentamethylpiperid-4-yl)-N,N'—bis-(di-sec.-butyl-carbamoyl)-ethylenediamine

| | |
|---|---|
| 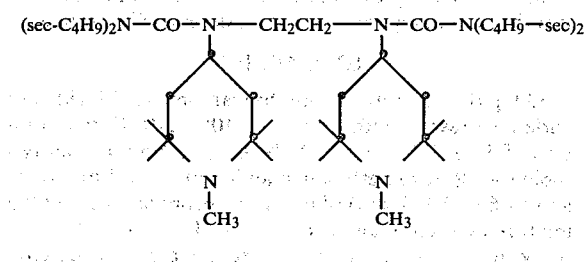 | melting point 194–196° (compound No. 4) |

N,N'—bis-(2,2,6,6-tetramethylpiperid-4-yl)-N,N'—bis-(diphenylcarbamoyl)-hexamethylenediamine

| | |
|---|---|
| 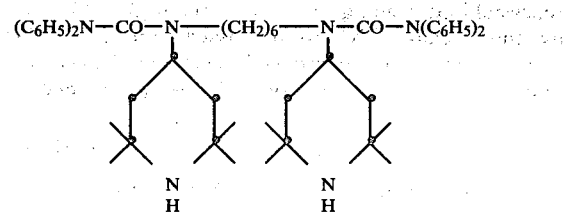 | melting point 250–252° (compound No. 5) |

N,N'—bis-(2,2,6,6-tetramethylpiperid-4-yl)-N,N'—bis-(dimethylcarbamoyl)-1,8-diamino-3,6-dioxa-octane

| | |
|---|---|
| 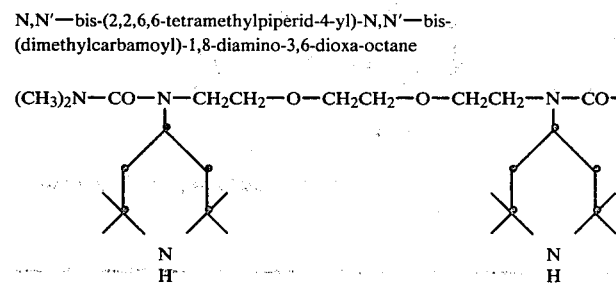 | melting point 70–71° (compound No. 6) |

N,N'—bis-(1,2,2,6,6-pentamethylpiperid-4-yl)-N,N'—bis-(dimethylcarbamoyl)-hexamethylenediamine

| | |
|---|---|
| 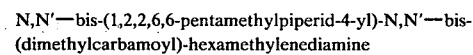 | melting point 136–137° (compound No. 7) |

N,N'—bis-(1,2,2,6,6-pentamethylpiperid-4-yl)-N,N'—bis-(diethylcarbamoyl)-trimethylenediamine -continued (C₂H₅)₂N—CO—N—CH₂CH₂CH₂—N—CO—N(C₂H₅)₂

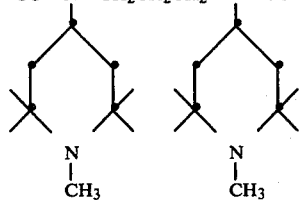

(compound No. 8)

viscous oil, analysis:  calculated  C 68.5%  H 11.5%  N 14.5%
                        found       C 68.5%  H 11.7%  N 14.5%

N—bis (1,2,2,6,6-pentamethylpiperid-4-yl)-N'—dimethylurea

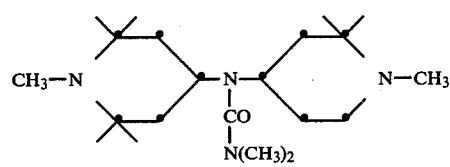

melting point 156–157°
(compound No. 9)

N,N'—bis-(2,2,6,6-tetramethylpiperid-4-yl)-N,N'—bis-
(hexamethyleneiminocarbonyl)-hexamethylenediamine

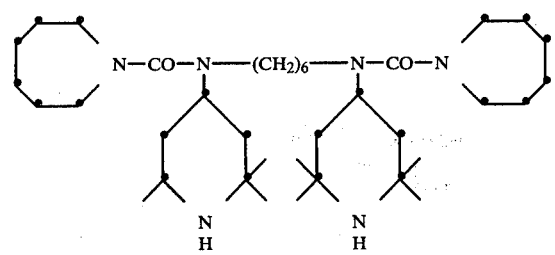

melting point 98–100°
(compound No. 10)

N,N'—bis-(2,2,6,6-tetramethylpiperid-4-yl)-N,N'—bis-
(morpholinocarbonyl)-hexamethylenediamine

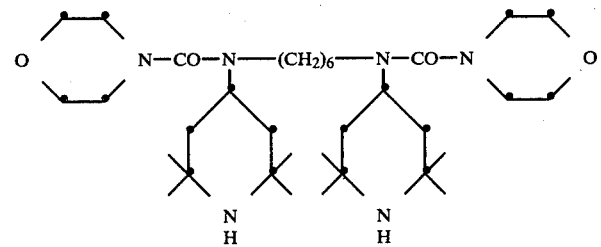

melting point 123–124°
(compound No. 11)

N,N'—bis-(2,2,6,6-tetramethylpiperid-4-yl)-N,N'—bis-
(diallylcarbamoyl)-hexamethylenediamine (CH₂=CH—CH₂)₂—N—CO—N—(CH₂)₆—N—CO—N(CH₂CH=CH₂)₂

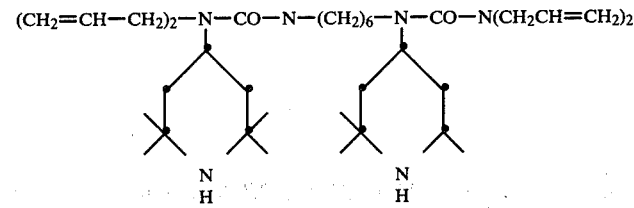

melting point 74–74°
(compound No. 12)

N,N'—bis-(2,2,6,6-tetramethylpiperid-4-yl)-N,N'—bis-
(dicyclohexylcarbamoyl)-hexamethylenediamine

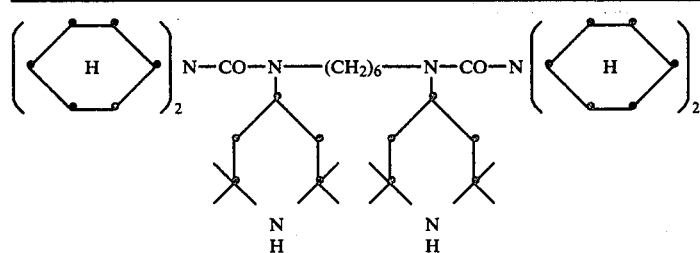

melting point 216–217°
(compound No. 13)

N—bis-(1,2,2,6,6-pentamethylpiperid-4-yl)-N'—di-sec.-butyl-urea

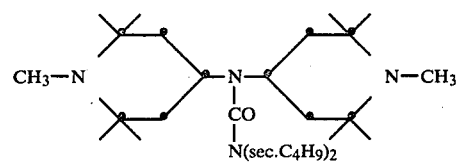

melting point 100–102°
(compound No. 14)

N—dodecyl-N—(2,2,6,6-tetramethylpiperid-4-yl)-N'—dimethyl-urea

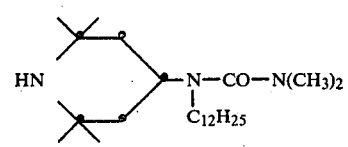

boiling point 190°/0.03 mm Hg (bulb tube)
(compound No. 15)

N—butyl-N—(1,2,2,6,6-pentamethylpiperid-4-yl)-N'—dioctyl-urea

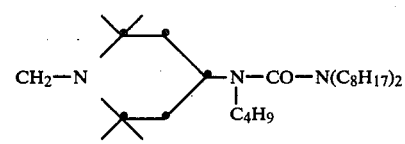

boiling point 205°/0.01 mm Hg (bulb tube)
(compound No. 16)

N,N'—bis-(1,2,2,6,6-tetramethylpiperid-4-yl)-N,N'—bis-(methylmethoxycarbamoyl)-trimethylenediamine

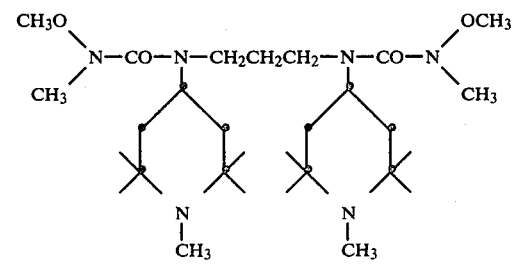

(compound No. 17)

| Elementary analysis | calculated: | C 62.78 | H 10.54 | N 15.15% |
|---|---|---|---|---|
| C29H58N6O4 | found: | C 62.5 | H 10.8 | N 14.9% |

EXAMPLE 2

26.9 g (0.05 mol) of N,N'-bis-(dimethylcarbamoyl)-N,N'-bis-(2,2,6,6-tetramethyl-4-piperidyl)-hexamethylenediamine (prepared according to Example 1), 18.2 g (0.15 mol) of allyl bromide, 16.6 g of powdered potassium carbonate, 0.5 g of powdered potassium iodide and 70 ml of ethyl methyl ketone are stirred for 24 hours at about 72°–74° (reflux temperature) in a nitrogen atmosphere. The reaction mixture is then filtered to remove the inorganic salts, the solvent is removed from the filtrate in vacuo and the crude compound is crystallised from pentane, by which means N,N'-bis-(dimethylcarbamoyl)-N,N'-bis-(1-allyl-2,2,6,6-tetramethylpiperid-4-yl)-hexamethylenediamine with a melting point of 96°–98° C. is obtained. Elementary analysis: C36H68N6O2 calculated: C, 70.08; H, 11.11; N, 13.62; O, 5.19%; found: C, 69.9; H, 11.3; N, 13.5; O, 5.1%.

(compound No. 18)

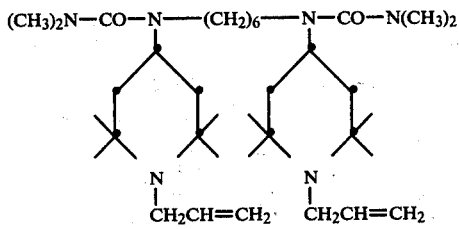

elementary analysis: $C_{48}H_{80}N_6O_2$ calculated: C, 75.56; H, 10.43; N, 10.87%; found: C, 75.7; H, 10.4; N, 10.9%.

(compound No. 22)

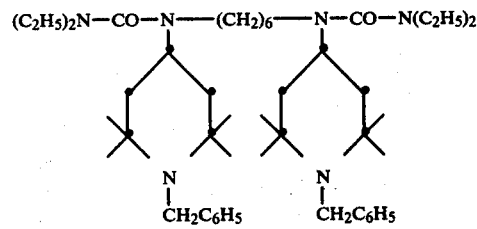

The following compounds are prepared analogously:

| | |
|---|---|
| N—bis-(1-allyl-2,2,6,6-tetramethylpiperid-4-yl)-N'—dimethylurea 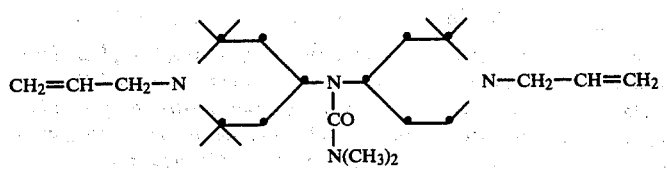 | melting point 88.5–90° (compound No. 19) |
| N,N'—bis-(1-allyl-2,2,6,6-tetramethylpiperid-4-yl)-N,N'—bis-(diethylcarbamoyl)-hexamethylenediamine 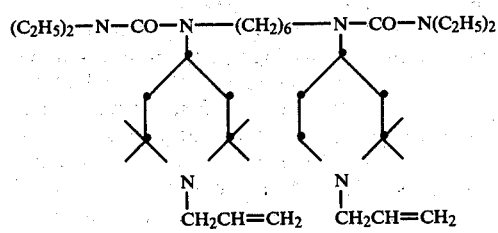 | melting point 68–69° (compound No. 20) |
| N,N'—bis-(1-allyl-2,2,6,6-tetramethylpiperid-4-yl)-N,N'—bis-(dicyclohexylcarbamoyl)-hexamethylenediamine 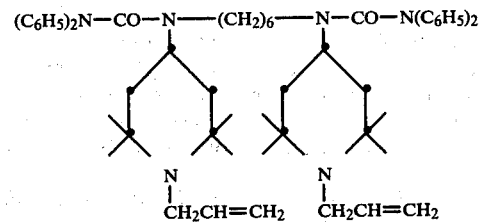 | melting point 172–173° (compound No. 21) |

EXAMPLE 3

17.6 g (0.13 mol) of diethylcarbamoyl chloride are added dropwise at 110°–120°, with stirring, to a solution of 34.6 g (0.06 mol) of N,N'-bis-(1-benzyl-2,2,6,6-tetramethylpiperid-4-yl)-hexamethylenediamine (melting point: 101°–103°, prepared by reductive amination of 1-benzyl-2,2,6,6-tetramethyl-piperid-4-one with hexamethylenediamine) in 150 ml of xylene and 15 g of triethylamine. After a reaction time of 9 hours at about 115°, the reaction mixture is cooled to room temperature, diluted with toluene, washed repeatedly with water, dried over sodium sulfate and completely freed from the solvents in vacuo. The crude compound is further purified by chromatography on silica gel (eluant: diethyl ether) and is recrystallized from n-hexane, by which means pure N,N'-bis-diethylcarbamoyl-N,N'-bis-(1-benzyl-2,2,6,6-tetramethylpiperid-4-yl)-hexamethylenediamine is obtained. Melting point 123°–124°, The following compound is prepared analogously:

N,N'—bis-(2,2,6,6-tetramethylpiperid-4-yl)-N,N'—bis-(diethylcarbamoyl)-hexamethylenediamine (compound No. 23)

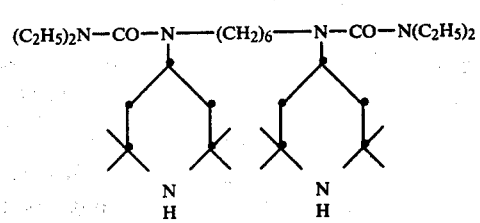

-continued melting point 142.5–144°

EXAMPLE 4

A solution of 16.5 g of n-butyl bromide in 10 ml of benzene is added dropwise in the course of 90 minutes, at 78°, to a vigorously stirred mixture (under a nitrogen atmosphere) of 9.65 g of N-(1,2,2,6,6-pentamethyl-piperidin-4-yl)-N'-dimethylurea (prepared from 4-amino-1,2,2,6,6-pentamethylpiperidine and dimethylcarbamoyl chloride: melting point 111°–112°), 40 ml of benzene, 5.6 g of sodium hydroxide, 11.06 g of potassium carbonate and 1.4 g of tetrabutylammonium hydrogen sulfate. The mixture is then stirred for a further 30 hours at 78°–80°. For working up, the white suspension is cooled to room temperature, 200 ml of diethyl ether are added, the resulting mixture is filtered, the filtrate is freed from the solvents in vacuo and the residue is purified by column chromatography on silica gel (60 Merck) (eluant: diethyl ether/methanol/triethylamine, 90:7:3), by which means pure N-butyl-N-(1,2,2,6,6-pentamethylpiperid-4-yl)-N'-dimethylurea with a melting point of 83°–85° is obtained (crystallised from acetonitrile). $C_{17}H_{35}N_3O$ (281.47): calculated: C, 68.64; H, 11.86; N, 14.13%; found: C, 68.5; H, 11.6; N, 14.1%.

(compound No. 24)

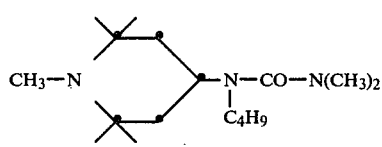

EXAMPLE 5

A solution of 29.7 g (0.21 mol) of redistilled 2,2,6,6-tetramethylpiperidine in 50 ml of xylene is added dropwise in the course of 1.5 hours, at −40°, to 40.2 g of a 25.7% solution of phosgene in xylene (0.105 mol), with stirring and under an inert gas atmosphere. After adding the amine, the mixture is stirred for a further 4 hours at −10° and for 18 hours at −5° to 0°. The 2,2,6,6-tetramethylpiperidinocarboxylic acid chloride which is thus obtained is not isolated but is now treated with a solution of 19.73 g (0.05 mol) of N,N'-bis-(2,2,6,6-tetramethyl-piperid-4-yl)-hexamethylenediamine and 20.4 ml (0.12 mol) of diisopropyl-ethylamine in 50 ml of xylene, this solution being added in the course of 2 hours, at −10°. After stirring for a further 18 hours at room temperature and for 6 hours at 50° C., the reaction mixture is cooled to room temperature, diluted with 300 ml of hexane and extracted four times with 150 ml of water, the organic phase is dried over sodium sulfate and the solvents are distilled off completely under a waterpump vacuum. The residue, which solidifies as crystals after a short time, is recrystallised from acetonitrile, and by this means pure N,N'-bis(2,2,6,6-tetramethylpiperid-4-yl)-N,N'-bis-(2,2,6,6-tetramethyl-piperidinocarbonyl)-hexamethylenediamine is obtained as a colourless compound with a melting point of 137°–139°.

(compound No. 25)

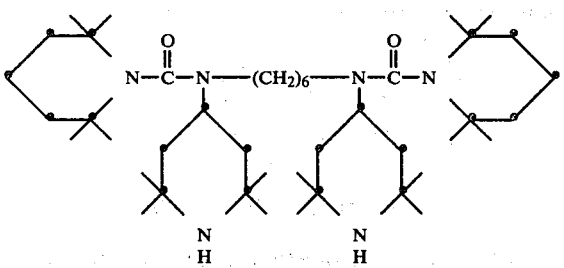

Elementary analysis: $C_{44}H_{84}N_6O_2$ calculated: N, 11.54%; found: N, 11.5%.

EXAMPLE 6

Stabilisation of polypropylene against light 100 parts of polypropylene powder (Moplen, fibre grade, from Montedison) are homogenised with 0.2 part of octadecyl β-(3,5-di-tert.-butyl-4-hydroxyphenyl)-propionate, 0.1 part of calcium stearate and 0.25 part of a stabiliser from Table 1 which follows, for 10 minutes in a Brabender plastograph at 200° C. The composition thus obtained is removed from the kneader as rapidly as possible and pressed in a toggle press to give a 2–3 mm thick sheet. Part of the resulting pressed blank is cut out and pressed between two high-gloss hard aluminum foils for 6 minutes at 260°, using a hand hydraulic laboratory press, to give a 0.1 mm thick film, which is immediately quenched in cold water. Cut pieces are now punched from this film and exposed in a Xenotest 1,200. These test pieces are removed from the exposure apparatus at regular intervals and their carbonyl content is tested in a IR spectrophotometer. The increase in the carbonyl extinction at 5.85 μm during exposure is a measure of the photo-oxidative degradation of the polymer (see Balaban et al., J. Polymer Sci., Part C; 22, 1,059–1,071 (1969)) and, according to experience, is associated with a deterioration of the mechanical properties of the polymer. The time taken to reach a carbonyl extinction of about 0.3, at which the comparison film is brittle, is taken as a measure of the protective effect.

The ratio of this exposure time to the exposure time of a blank sample without light stabiliser is the protection factor PF.

$$PF = \frac{\text{exposure time for sample}}{\text{exposure time for blank}}$$

The following table gives the protection factors for the light stabilisers testedd.

| Light stabiliser used | | Light protection factor PF |
|---|---|---|
| without | | 1 |
| Compound No. | 1 | 12 |
| | 2 | 13.8 |
| | 3 | 15.7 |
| | 18 | 8.4 |
| | 19 | 13.0 |
| | 20 | 8.7 |
| | 22 | 6.9 |

What is claimed is:

1. A compound of the formula I

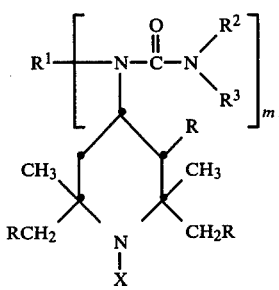

in which m is 1, 2, 3 or 4, X is H, O, $C_1$–$C_{18}$-alkyl, $C_3$–$C_5$-alkenyl, propargyl, $C_7$–$C_{12}$-phenylalkyl or a group of the formula —CO—$C_1$–$C_8$-alkyl, —CO—$C_2$–$C_3$-alkenyl, —CO—O—$C_1$–$C_{10}$-alkyl or —CO—N—($C_1$–$C_{10}$-alkyl)$_2$, R is hydrogen and $R^1$, if m is 1, is $C_1$–$C_{18}$-alkyl, $C_3$–$C_5$-alkenyl, $C_3$–$C_4$-alkynyl, $C_5$–$C_6$-cycloalkyl, $C_7$–$C_{18}$-aralkyl, $C_6$–$C_{12}$-aryl or a group of the formula II

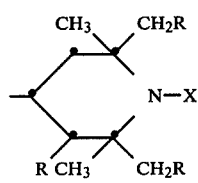

or, if m is 2, is $C_2$–$C_{20}$-alkylene, $C_4$–$C_{12}$-mono- or -dioxaalkylene, a

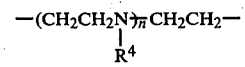

or —(CH$_2$)$_3$—N(R$^5$)—(CH$_2$)$_3$-group, cyclohexylene, xylylene, hexahydroxylylene or a

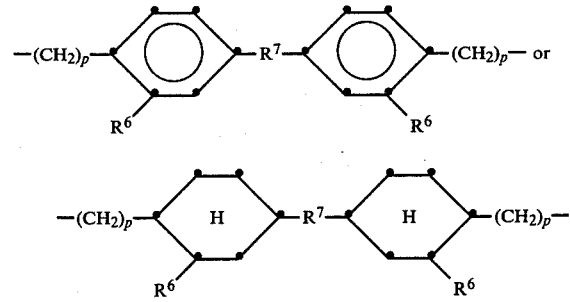

group, in which $R^4$ is hydrogen, $C_1$–$C_4$-alkyl, allyl, benzyl or a

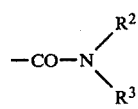

group, n is an integer from 1 to 5, $R^5$ is $C_1$–$C_{12}$-alkyl, phenyl or cyclohexyl, p is nought or 1, $R^6$ is hydrogen or methyl and $R^7$ is —CH$_2$— or >C(CH$_3$)$_2$, or $R^1$, if m is 3, is a

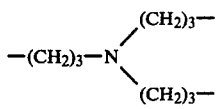

radical and if m is 4 is a radical of the formula

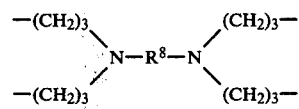

in which $R^8$ is $C_2$–$C_{20}$-alkylene, cyclohexylene or xylylene, and $R^2$ and $R^3$ independently of one another are $C_1$–$C_{12}$-alkyl, cyclohexyl, $C_3$–$C_5$-alkenyl, propargyl, $C_7$–$C_{12}$-phenylalkyl or $C_6$–$C_{12}$-aryl, and $R^2$ can also be $C_1$–$C_4$-alkoxy, or $R^2$ and $R^3$ together form $C_4$–$C_9$-alkylene or 3-oxa-1,5-pentylene.

2. A compound according to claim 1, of the formula I, in which m is 1 or 2, R is hydrogen, X is hydrogen, $C_1$–$C_8$-alkyl, allyl or benzyl and $R^1$, if m is 1, is $C_1$–$C_{12}$-alkyl or a group of the formula II, and, if m is 2, is $C_2$–$C_{10}$-alkylene or $C_4$–$C_6$-oxaalkylene, 1,4-cyclohexylene or a

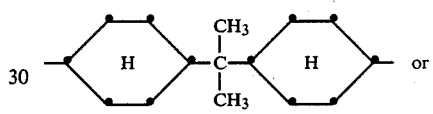

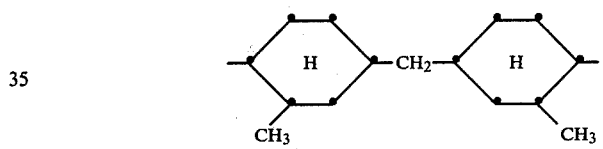

group, and $R^2$ and $R^3$ independently of one another are $C_1$–$C_{10}$-alkyl, phenyl, cyclohexyl, allyl or benzyl, or $R^2$ and $R^3$ together are $C_4$–$C_6$-alkylene or 3-oxa-1,5-pentylene.

3. A compound according to claim 1, of the formula I, in which m is 1 or 2, R is hydrogen, X is hydrogen, $C_1$–$C_4$-alkyl, allyl or benzyl and $R^1$, if m is 1, is $C_1$–$C_4$-alkyl or a group of the formula II, and if m is 2 is $C_2$–$C_6$-alkylene or $C_4$–$C_6$-oxaalkylene, and $R^2$ and $R^3$ are $C_1$–$C_{12}$-alkyl, phenyl, cyclohexyl or allyl, or $R^2$ and $R^3$ together are $C_4$–$C_6$-alkylene or 3-oxa-1,5-pentylene.

4. The compounds according to claim 1: N-bis-(2,2,6,6-tetramethylpiperid-4-yl)-N'-dimethylurea, N-bis-(1-allyl-2,2,6,6-tetramethylpiperid-4-yl)-N'-dimethylurea, N-dodecyl-N-(2,2,6,6-tetramethylpiperid-4-yl)-N'-dimethylurea, N,N'-bis-(2,2,6,6-tetramethylpiperid-4-yl)-N,N'-bis-(dimethylcarbamoyl)-hexamethylenediamine and N,N'-bis-(1-allyl-2,2,6,6-tetramethylpiperid-4yl)-N,N'-bis-(dimethylcarbamoyl)-hexamethylenediamine.

5. A polymer composition stabilised against the action of light, the said composition containing 0.01 to 5% by weight of at least one compound of the formula I of claim 1.

6. A polymer composition according to claim 5, wherein the polymer is a polyolefin, a styrene polymer or a polyurethane.

7. A polymer composition according to claim 5, wherein the polymer is a lacquer resin.

* * * * *